United States Patent
Chau et al.

(10) Patent No.: US 9,464,986 B2
(45) Date of Patent: Oct. 11, 2016

(54) MULTIPLEX FIBER OPTIC BIOSENSOR AND DETECTION METHOD BY USING THE SAME

(71) Applicant: National Chung Cheng University, Chia-Yi (TW)

(72) Inventors: Lai-Kwan Chau, Chiayi (TW); Chen-Han Huang, Tainan (TW); Hisng-Ying Lin, Kaohsiung (TW); Yu-Chia Liu, Minxiong Township (TW)

(73) Assignee: National Chung Cheng University, Min-Hsiung Township (TW)

( * ) Notice: Subject to any disclaimer, the term of this patent is extended or adjusted under 35 U.S.C. 154(b) by 55 days.

(21) Appl. No.: 14/164,935

(22) Filed: Jan. 27, 2014

(65) Prior Publication Data

US 2015/0211993 A1   Jul. 30, 2015

(51) Int. Cl.
*G01N 21/55* (2014.01)
*G01N 21/552* (2014.01)
*G01N 21/77* (2006.01)

(52) U.S. Cl.
CPC ........ *G01N 21/554* (2013.01); *G01N 21/7703* (2013.01); *G01N 2021/7793* (2013.01)

(58) Field of Classification Search
None
See application file for complete search history.

(56) References Cited

U.S. PATENT DOCUMENTS 8,355,134 B2* 1/2013 Chau et al. ............... 356/445
2006/0269966 A1* 11/2006 Miyamoto et al. ........ 435/7.1

OTHER PUBLICATIONS

Lin et al, "Multiplex fiber-optic biosensor using multiple particle plasmon resonances", Jan. 31, 2012, Proc. SPIE 8351, Third Asia Pacific Optical Sensors Conference, 83512S.*

* cited by examiner

*Primary Examiner* — Kara E Geisel
*Assistant Examiner* — Amanda Merlino
(74) *Attorney, Agent, or Firm* — Wang Law Firm, Inc.

(57) ABSTRACT

A multiplex fiber optic biosensor including an optical fiber, a plurality of noble metal nanoparticle layers, a plurality of light sources and a light source function generator is disclosed. The optical fiber includes a plurality of sensing regions which are unclad regions of the optical fiber so that the fiber core is exposed, wherein the noble metal nanoparticle layers are set in each sensing regions. The light sources emit light with different wavelengths, and the noble metal nanoparticle layers absorb the lights with different wavelengths, respectively. The light sources emit the lights in different timing sequences or different carrier frequencies, wherein when the lights propagate along the optical fiber in accordance with the different timing sequences or the different carrier frequencies, a detection unit detects particle plasmon resonance signals produced by interactions between the different noble metal nanoparticle layers and the corresponding analytes.

6 Claims, 20 Drawing Sheets

MULTIPLEX FIBER OPTIC BIOSENSOR AND DETECTION METHOD BY USING THE SAME

BACKGROUND OF THE INVENTION

1. Field of the Invention

The present invention generally relates to a biosensor and detection method by using the same, in particular to a multiplex fiber optic biosensor and detection method by using the same.

2. Description of the Related Art

A fiber optic biosensor directs light waves produced by light sources to a to-be-detected region by means of optical fiber, and physical or chemical quantity in the to-be-detected region, such as variations in stress, strain, temperature, refractive index and molecular concentration will cause change of light wave's characteristic, so the variations in the physical or chemical quantity in the to-be-detected region can be obtained by the change of light wave's characteristic. When the sensing signal of a fiber optic sensor is transmitted in optical fiber, there are less electromagnetic noise and magnetic interference, and influence of ionization radiation is evitable through radiation processing, so that it is applicable to tough environment, such as nuclear power plant. Moreover, the same optical fiber can be served as a sensor and signal transduction line, and size of the sensor is usually smaller than traditional one, so that it can be placed in tiny region or zone where is not easy to reach.

A fiber optic sensor excites and transmits signal by means of light without using electric current or voltage, so it is away from danger to electric shock and applicable to medical measurement. The material of optical fiber has characteristics of corrosion resistance so to fit into being used in deep sea engineering as well as chemical corrosion environment, and also with better biological compatibility. Because the temperature tolerance of glass optical fiber is better than that of metal strain gauges, and both the long-term stability and fatigue life of glass optical fiber are better than resistance strain gauge, it is suitable to be used for long-term monitoring works. As optical fiber has been utilizing in long distance communication, the technology related to fiber optic sensor is therefore easy to be conducted for long distance measurements. In addition, the Wavelength-Division Multiplexing in optical communication also contributes to the multipoint measurement in the same optical fiber; consequently, fiber optic sensors have been widely used in fields pertaining to aerospace, medicine, chemistry, geotechnical engineering and civil engineering and so on and so forth.

With reference to FIG. 1 for a schematic diagram of a known fiber optic biosensor. Firstly, when light sources of multiple wavelengths $\lambda_1, \lambda_2, \lambda_3 \ldots \lambda_n$ are coupled to an optical fiber 100, the lights with different wavelengths are separated by grating, prism, or spectrograph 110, and signals with different wave bands are received by means of Charge Coupled Devices (CCDs), photodiodes, photomultiplier tubes, or an array-based detector. The known fiber optic biosensor, however, has the following disadvantages: when light signals of multiple wavelengths are being separated via grating, prism, or spectrograph 110, the signals cannot be well-resolved if the wavelengths are too close, resulting in inaccuracy of measurement. Furthermore, such a design requires that the quantity of the detection units has to be equal to the quantity of light sources which emit lights with different wavelengths. As a result, the total cost of the detection units will increase if a sample has multiple analytes to be analyzed; besides, it is also inevitable to raise the cost due to the usage of spectrometer.

Recently, the development of nanomaterials becomes more and more important in relevant research and applications, such as photoelectronics, energy, biomedical sensing instrument and so on. The reason for the prosperity lies in that the nanomaterials typically have special characteristics as compared to the bulk materials. One special property of noble metal nanoparticles, which is "the free electron cloud on surface of noble metal nanoparticle is excited by electromagnetic field with specific frequency and further responses in collective dipole resonance, but the vivid electron clouds are localized at the nanoparticle," is called as Localized Surface Plasmon Resonance (LSPR) or called as Particle Plasmon Resonance (PPR). When the noble metal nanoparticle senses the variation in refractive index of the medium surrounding it, the frequency and intensity of the particle plasmon resonance band will also be changed. By observing the absorption band of noble metal nanoparticle, it can be found that when the refractive index raises, the absorption band of the particle plasmon resonance will move to longer wavelength and the absorbance will be increased; besides, as far as the characteristic of scattering light is concerned, it can be found that when the refractive index raises, the band of the scattering light will also move to longer wavelength and the intensity of light will be increased. Finally, when a specific molecular recognition unit is modified on the nanoparticle surface to have sensing ability of specificity, and by analyzing the relationship between either the frequency or intensity of the resonance band and the concentration of the analyte, the corresponding measurement method is thereby established. The method mainly depends on modifying the noble metal nanoparticles on the optical fiber so as to form a noble metal nanoparticle layer, wherein the noble metal nanoparticle layer is composed of one of spherical noble metal nanoparticle, square noble metal nanoparticle, pyramidal noble metal nanoparticle, rod-shaped noble metal nanoparticle and shell-shaped noble metal nanoparticle, and the noble metal nanoparticles are not connected with each other. The noble metal may be gold, silver or platinum. The absorption variation in evanescent wave of the noble metal nanoparticle plasmon resonance can be accumulated by consecutive multiple total internal reflections along the optical fiber, so as to increase the PPR signal and strengthen the sensing sensitivity. After combining with molecular recognition unit, it is of specificity together with high sensing sensitivity, so that it has a potential of being developed as real time sensing instrument.

SUMMARY OF THE INVENTION

Therefore, the purpose of the present invention is to provide a multiplex fiber optic biosensor and detection method by using the same, which lights propagate along the optical fiber in accordance with different timing sequences or different carrier frequencies, and then a detection unit is used to detect as well as analyze the variation in the particle plasmon resonance signals.

The multiplex fiber optic biosensor of the present invention comprises: an optical fiber, a plurality of noble metal nanoparticle layers, a plurality of light sources and a light source function generator. Wherein, the optical fiber includes a plurality of sensing regions, and the sensing regions are unclad regions of the optical fiber so that the fiber core is exposed and different kinds of noble metal nanoparticle layers are set in different sensing regions. In addition, the light sources emit lights with different wavelengths in accordance with different timing sequences or different carrier frequencies based on the function generated by the light source function generator, respectively; and the noble metal nanoparticle layers absorb the lights with different wavelengths, respectively. Wherein, when the lights with different wavelengths propagate along the optical fiber in accordance with the different timing sequences or the different carrier frequencies, a detection unit is used to detect the variation in particle plasmon resonance signals produced by interactions between the different noble metal nanoparticle layers and the corresponding analytes. Preferably, the light sources are light-emitting diodes (LEDs).

Wherein, the multiplex fiber optic biosensor of the present invention preferably further comprises a timing control unit, and the light source function generator is electrically connected to the timing control unit, so that the light sources emit lights in the different timing sequences.

Preferably, the light source function generator is electrically coupled to the detection unit and transmits the function to the detection unit, so as to analyze the variation in particle plasmon resonance signals in each different channel by means of trigger.

In addition, the detection unit preferably comprises: a photodiode, a current amplifier, an analog/digital converter and a computer device. Wherein, the photodiode is used to detect the particle plasmon resonance signals. Furthermore, the current amplifier is electrically connected to the photodiode to amplify the particle plasmon resonance signals, and the analog/digital converter is electrically connected to the current amplifier to transform the particle plasmon resonance signals into digital signals; and the computer device is electrically connected to the current amplifier to receive as well as analyze the particle plasmon resonance signals.

Moreover, the computer device receives the particle plasmon resonance signals by a universal serial bus (USB).

According to another purpose of the present invention, it provides a multiplex fiber optic biosensor detection method comprising the following steps of: providing an optical fiber and a plurality of noble metal nanoparticle layers, wherein the optical fiber comprises a plurality of sensing regions, and the sensing regions are unclad regions of the optical fiber so that the fiber core is exposed, and the different noble metal nanoparticle layers are set in the different sensing regions; providing a light source function generator and a plurality of light sources, wherein the light source function generator generates a function, so that the light sources emit lights in accordance with different timing sequences or different carrier frequencies based on the function, and the noble metal nanoparticle layers absorb lights with different wavelengths, respectively; and providing a detection unit, wherein, when the lights with different wavelengths propagate along the optical fiber in accordance with the different timing sequences or the different carrier frequencies, the detection unit is used to detect particle plasmon resonance signals produced by interactions between the different noble metal nanoparticle layers and the corresponding analytes. Preferably, the light sources are light-emitting diodes (LEDs).

Wherein, the multiplex fiber optic biosensor mentioned in the multiplex fiber optical biosensor detection method of the present invention preferably comprises a timing control unit, and the light source function generator is electrically connected to the timing control unit, so that the light sources emit lights in accordance with the different timing sequences.

Preferably, the light source function generator is electrically coupled to the detection unit and transmits the function to the detection unit, so as to analyze the particle plasmon resonance signals in each different channel by means of trigger.

In addition, the detection unit mentioned in the multiplex fiber optic biosensor detection method of the present invention preferably comprises: a photodiode, a current amplifier, an analog/digital converter and a computer device. Wherein, the photodiode is used to detect the particle plasmon resonance signals. Furthermore, the current amplifier is electrically connected to the photodiode to amplify the particle plasmon resonance signals; the analog/digital converter is electrically connected to the current amplifier to transform the particle plasmon resonance signals into digital signals; and the computer device is electrically connected to the current amplifier to receive as well as analyze the particle plasmon resonance signals.

Besides, the computer device receives the particle plasmon resonance signals by a universal serial bus (USB).

According to the aforementioned description, the particle plasmon resonance sensing device and the optical fiber structure in accordance with the present invention have the following advantages:

(1) The multiplex fiber optic biosensor and detection method by using the same of the present invention analyze wavelengths of lights without using spectrometer.

(2) The multiplex fiber optic biosensor and detection method by using the same of the present invention analyze the interactions of numerous nanomaterials with the corresponding analytes by using only one detection unit.

DETAILED DESCRIPTION OF THE PREFERRED EMBODIMENTS

Figure 1:
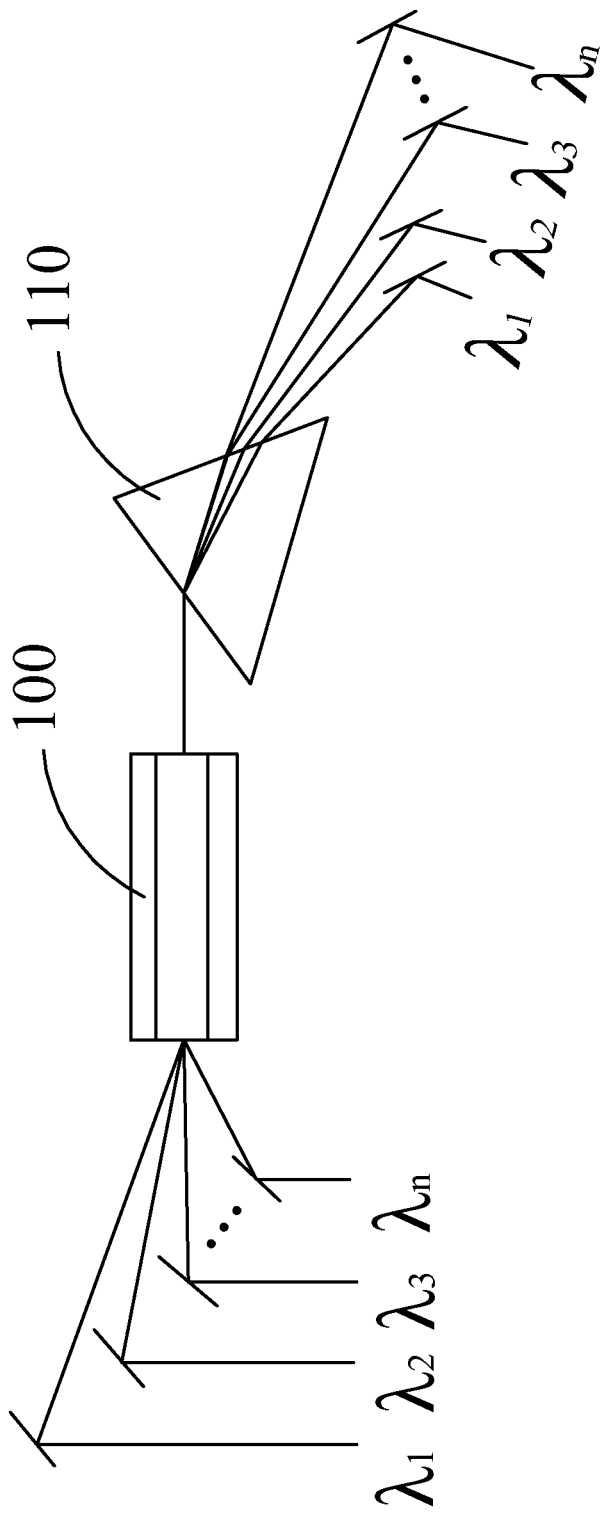
FIG. 1 is a schematic diagram of a known fiber optic biosensor.
Figure 2A:
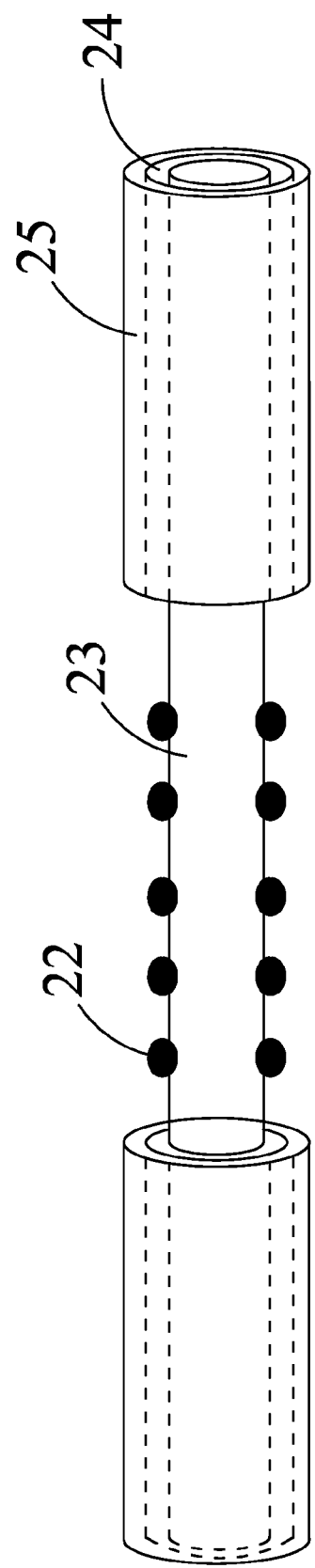
FIG. 2A is an exemplary schematic diagram showing an optical fiber with a fully unclad segment as one sensing region of a multiplex fiber optic biosensor in accordance with the present invention.
Figure 2B:
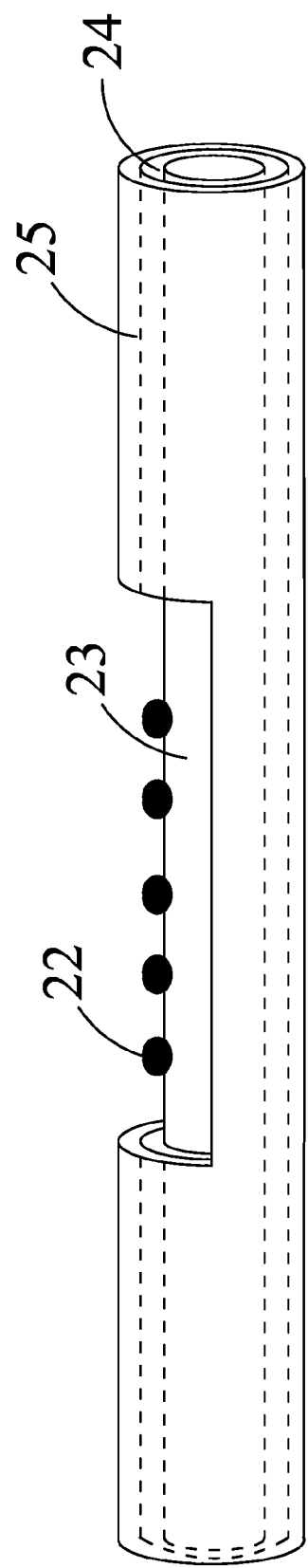
FIG. 2B is an exemplary schematic diagram showing an optical fiber with a partially unclad segment as one sensing region of a multiplex fiber optic biosensor in accordance with the present invention.
Figure 2C:
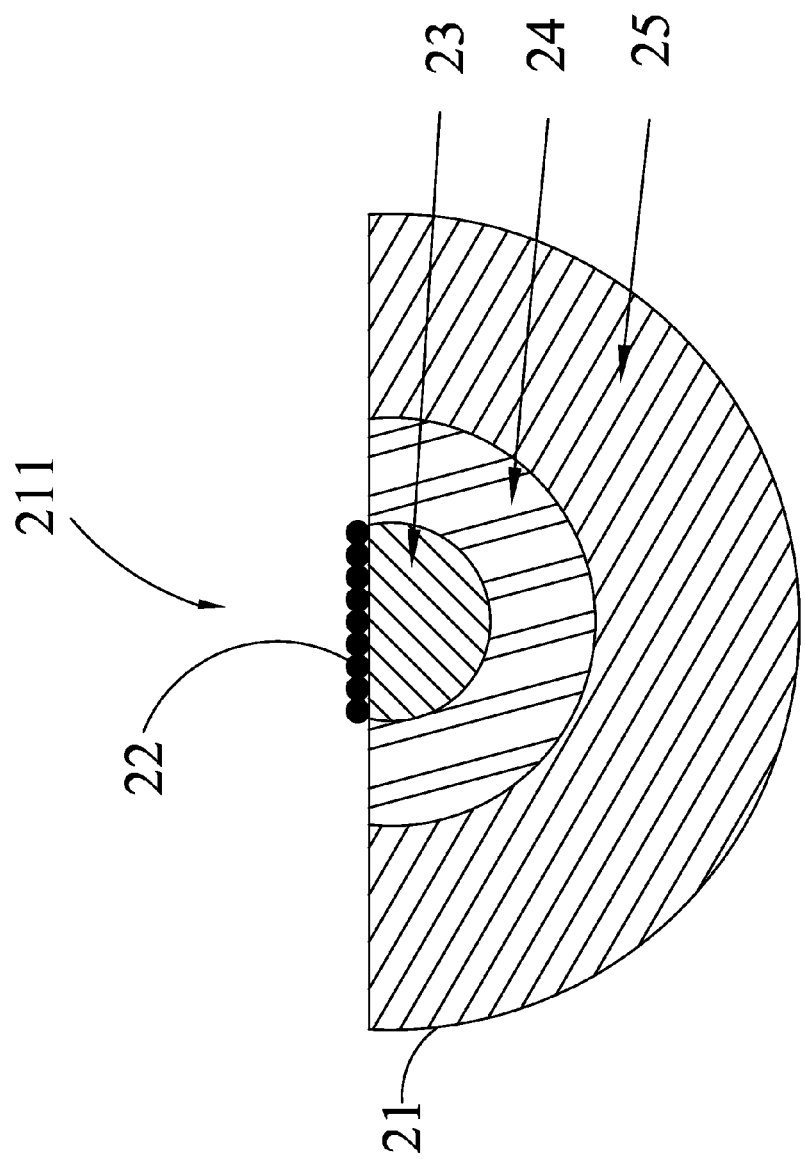
FIG. 2C is an exemplary cross-section diagram showing an optical fiber with part of fiber coating, fiber cladding and fiber core removed to form one sensing region of a multiplex fiber optic biosensor in accordance with the present invention.
Figure 3A:
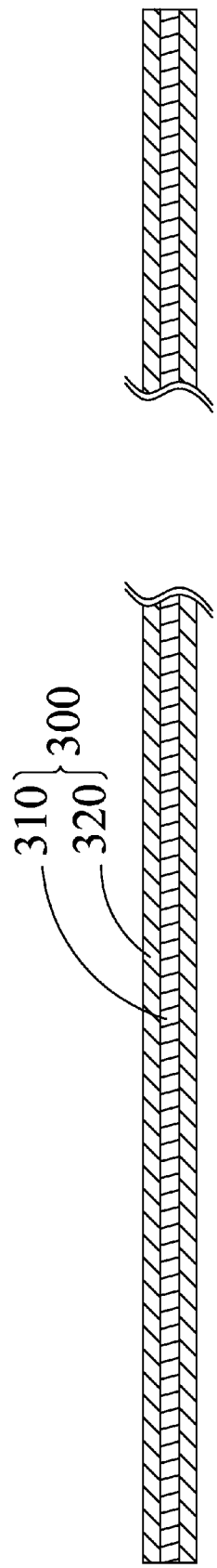
FIGS. 3A to 3F are schematic diagrams showing the manufacturing process of an optical fiber with a plurality of noble metal nanoparticle layers to produce a multiplex fiber optic biosensor in accordance with the present invention.
Figure 3B:
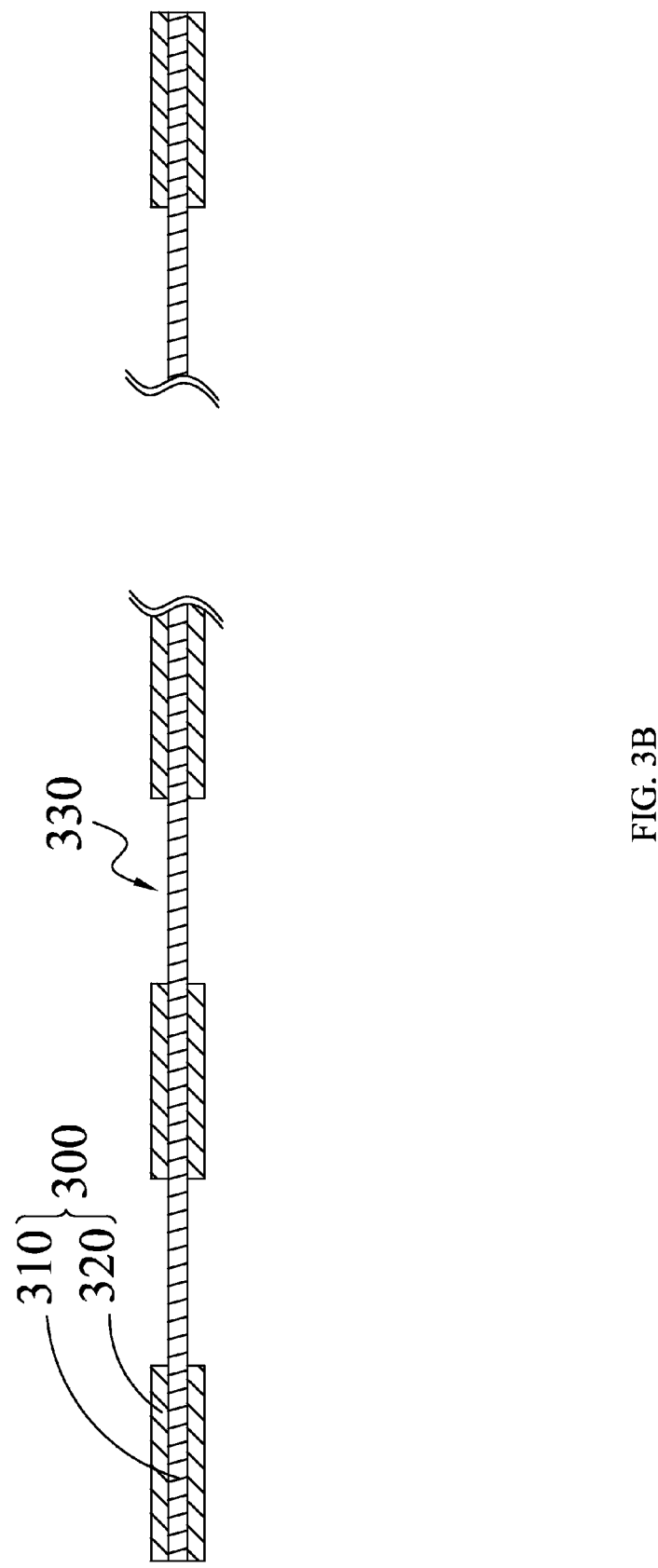
Figure 3C:
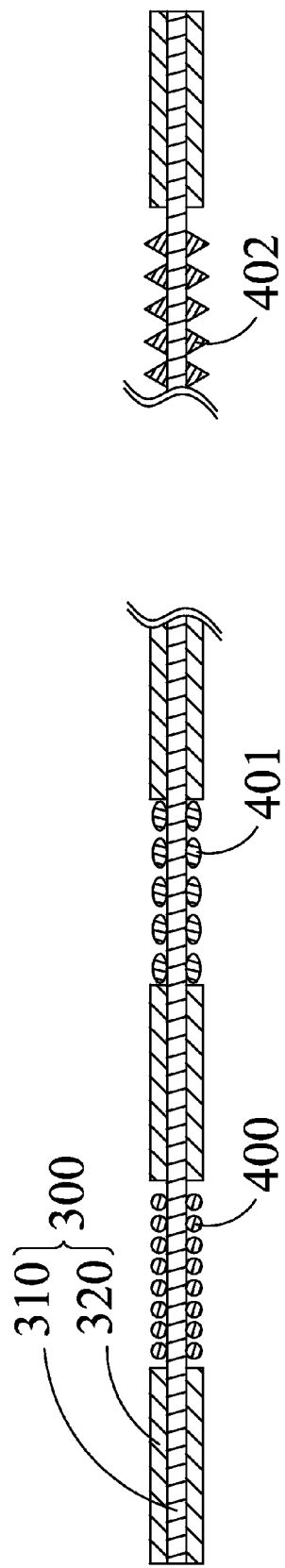
Figure 3D:
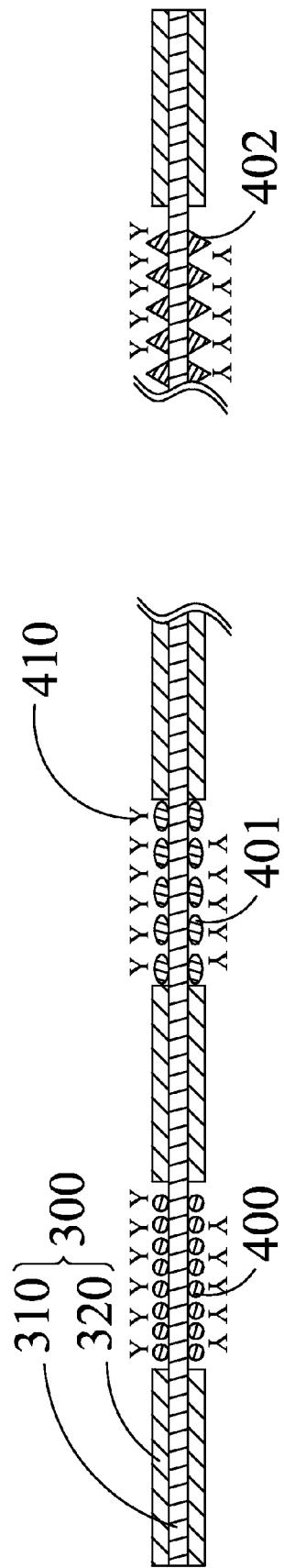
Figure 3E:
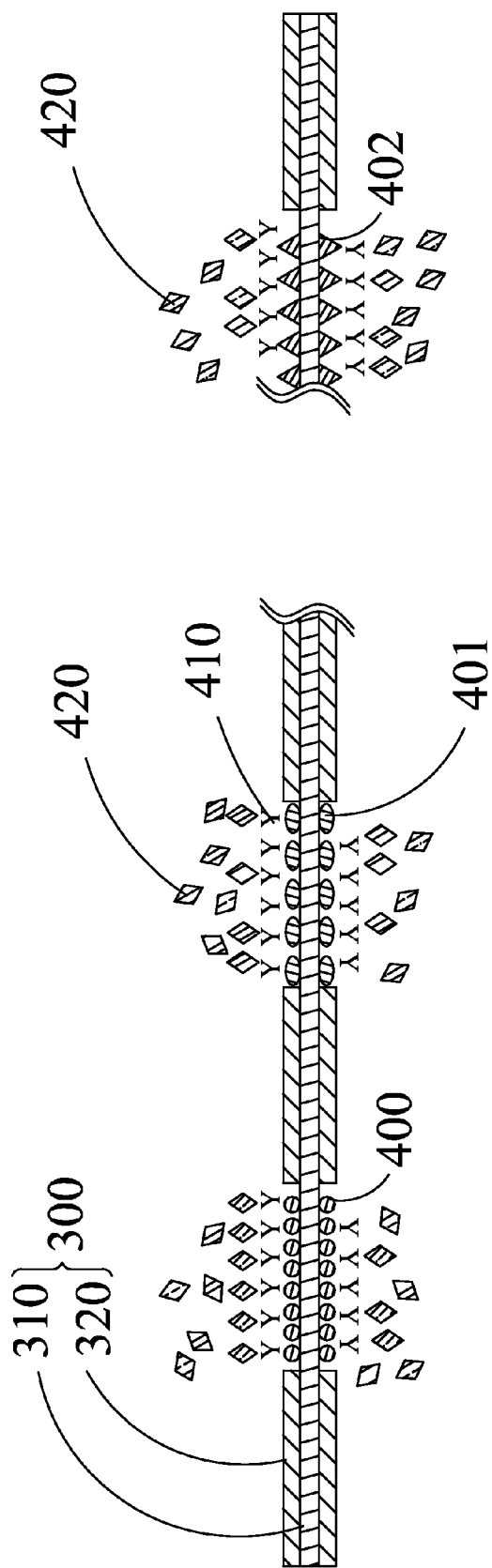
Figure 3F:
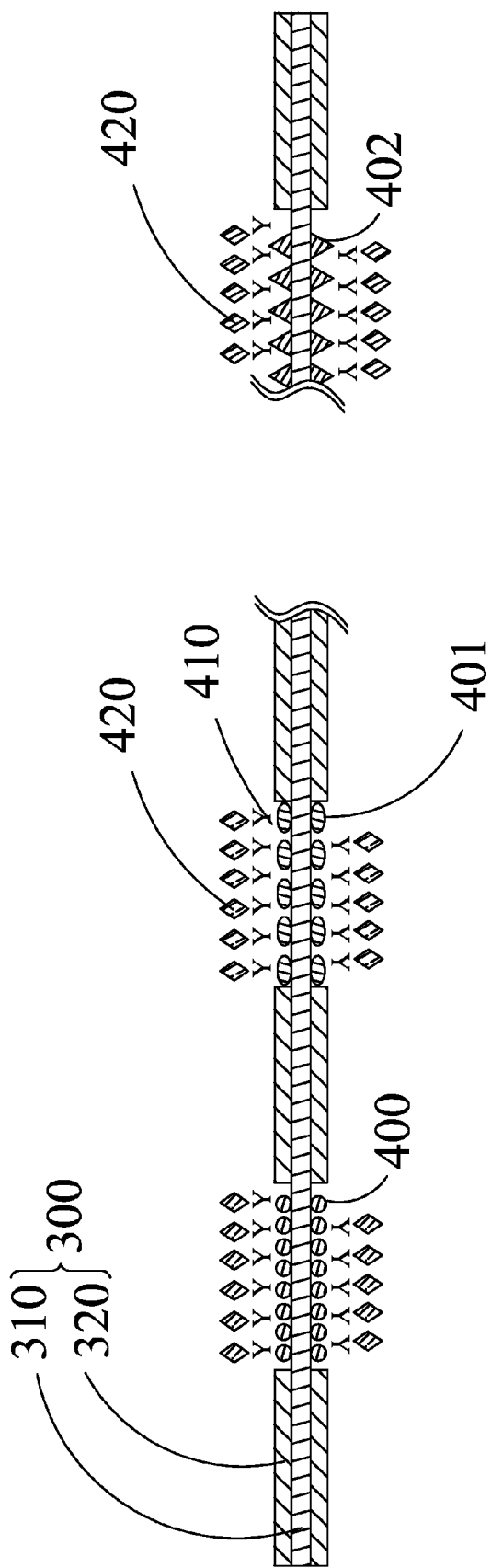

With reference to FIGS. 2A to 2C. FIG. 2A is an exemplary schematic diagram showing an optical fiber with a fully unclad segment as one sensing region of a multiplex fiber optic biosensor in accordance with the present invention; FIG. 2B is an exemplary schematic diagram showing an optical fiber with a partially unclad segment as one sensing region of a multiplex fiber optic biosensor in accordance with the present invention and FIG. 2C is an exemplary cross-section diagram showing an optical fiber with part of fiber coating, fiber cladding and fiber core removed to form one sensing region of a multiplex fiber optic biosensor in accordance with the present invention. As can be seen from FIGS. 2A to 2C, an optical fiber 21 may comprise a fiber core 23 and a cover layer, and the cover layer may comprise a fiber cladding 24 and a fiber coating 25, the sensing region of the optical fiber 21 may be a fully or partially unclad segment, and the optical fiber 21 comprises a plurality of sensing regions 211, and the sensing regions 211 are set in the side surface of the optical fiber 21. Wherein, the sensing region 211 is an unclad region of the optical fiber 21 so that the fiber core 23 of the optical fiber 21 is exposed.

Moreover, a plurality of noble metal nanoparticle layers 22 are set in the sensing regions 211, and the noble metal nanoparticle layers 22 may be composed of gold nanoparticle, sliver nanoparticle or platinum nanoparticle, and nanoparticle formed by the noble metal nanoparticle layers 22 may be pure nanoparticle. Wherein, when lights emitted by light sources propagate along the optical fiber 21, a detection unit detects particle plasmon resonance signals produced by interactions between the noble metal nanoparticle layers 22 and the corresponding analytes; and no matter the optical fiber has the fiber coating 25 or not, the optical fiber can be served as the sensing optical fiber 21 of particle plasmon resonance sensing device. The diameter of fiber core 23 of the sensing optical fiber 21 selected in present invention may be less than 1000 μm, and preferably, the range thereof may be 4 to 400 μm.

With reference to FIG. 3A to 3F for schematic diagrams showing the manufacturing process of an optical fiber with a plurality of noble metal nanoparticle layers to produce a multiplex fiber optic biosensor in accordance with the present invention. Firstly, the fiber cladding 320 of different segments of the optical fiber 300 are removed, so that the fiber core 310 is exposed to form a plurality of sensing regions 330, and different noble metal nanoparticle layers 400, 401, 402 are respectively modified on each of the plurality of sensing regions 330; and then chemical structure 410 (such as antigen or antibody) for sensing is modified on the different noble metal nanoparticle layers 400, 401, 402 in accordance with the type of to-be-measured analytes, and the sensing is thereby conducted in a sample containing the analytes 420. Because the aforementioned chemical structure 410 for sensing employs the substance (molecular recognition unit) which only reacts with a single analyte, hence, it is specific.

When the above optical fiber 300 and the noble metal nanoparticle layers 400, 401, 402 are prepared, the analysis of the analytes can be made. The multiplex fiber optic biosensor in accordance with the present invention conducts the analysis via two means.

Figure 4A:
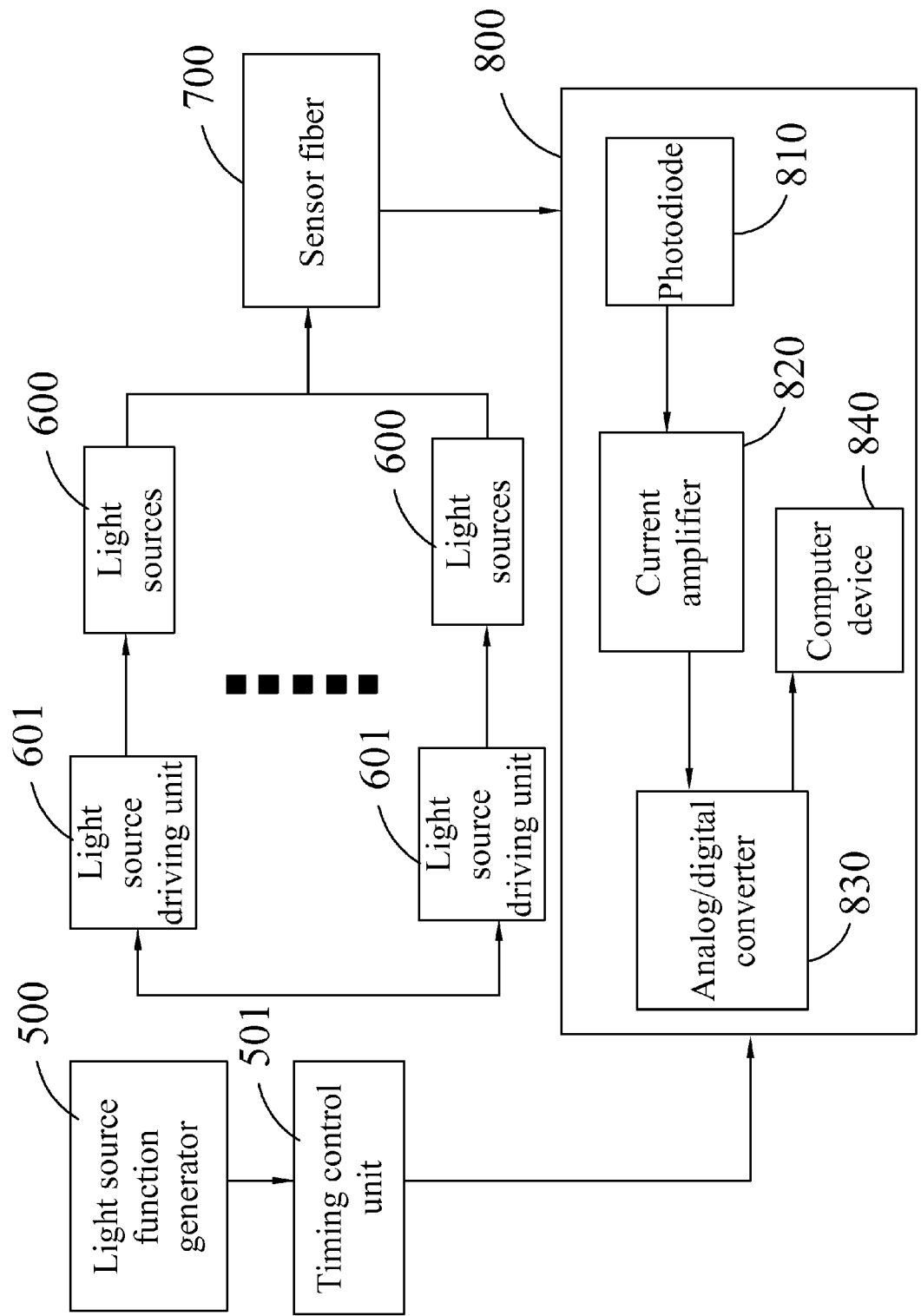
FIG. 4A is a schematic diagram showing the operation of a multiplex fiber optic biosensor in accordance with the present invention.
Figure 4B:
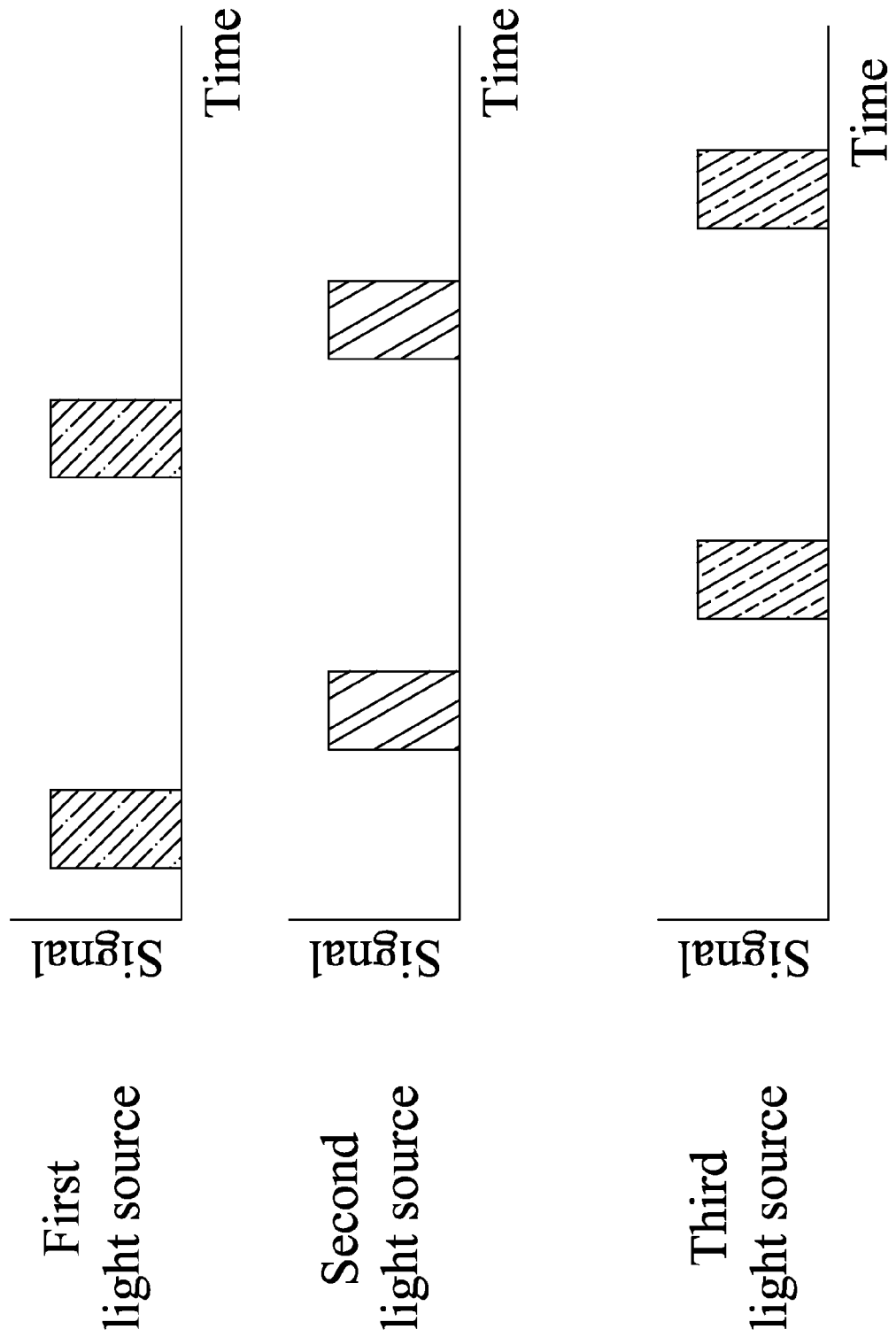
FIG. 4B is a schematic diagram showing the light sources of a multiplex fiber optic biosensor emit lights with different timing sequences in accordance with the present invention.
Figure 4C:
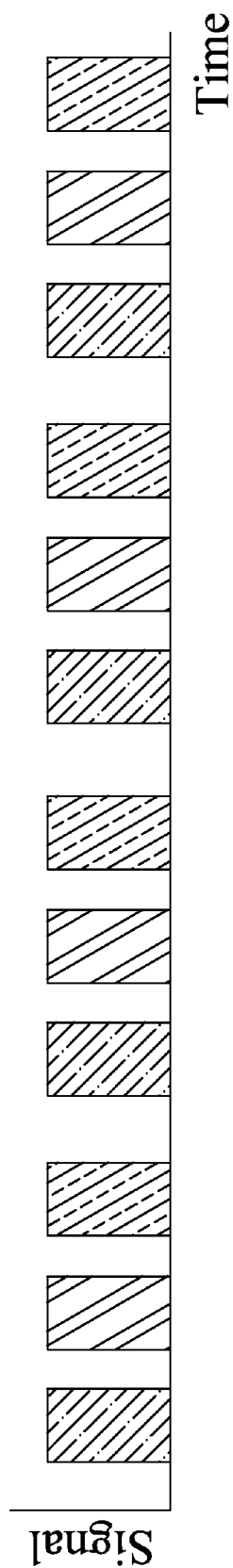
FIG. 4C is a schematic diagram showing the detection unit of a multiplex fiber optic biosensor receives particle plasmon resonance signals in accordance with the present invention.

Firstly, with reference to FIGS. 4A to 4C for the first means. FIG. 4A is a schematic diagram showing the operation of a multiplex fiber optic biosensor in accordance with the present invention, FIG. 4B is a schematic diagram showing the light sources of a multiplex fiber optic biosensor emit lights with different timing sequences in accordance with the present invention and FIG. 4C is a schematic diagram showing the detection unit of a multiplex fiber optic biosensor receives particle plasmon resonance signals in accordance with the present invention. A light source function generator 500 generates a function, so that a plurality of light sources 600 with different wavelengths emit lights in accordance with different timing sequences. Preferably, the light source function generator 500 is further electrically connected to a timing control unit 501 so as to calculate the elapsed time. And preferably, the light sources 600 are further electrically connected to a light source driving unit 601, and the light source driving unit 601 is electrically connected to the light source function generator 500 to receive the function, so that the light sources 600 emit lights in accordance with different timing sequences based on the function. For example, if the analytes have three components that needs to be analyzed, three timing points for emitting light are needed, more specifically, a first light source can emit light at second 1, second 4, second 7, and second 10 . . . etc., a second light source can emit light at second 2, second 5, second 8, and second 11 . . . etc., and a third light source can emit light at second 3, second 6, second 9, and second 12 . . . etc. It is noteworthy that the three components exampled here have to correspond to three light sources with different wavelengths, respectively, and the noble metal nanoparticle layers absorb the three lights with different wavelengths, respectively. In other words, the lights with different wavelengths are emitted by the three light sources in accordance with three different timing sequences, and each light is absorbed by the corresponding noble metal nanoparticle layer when the wavelength of the light matches the resonance wavelength of the noble metal nanoparticle layer, so as to generate three kinds of particle plasmon resonance signals. Wherein, it has to be mentioned specifically that the three lights with different wavelengths do not emit lights continuously, but only emit lights with the timing sequences designated by the function.

In addition, after the aforementioned three lights with different wavelengths passed through the optical fiber and the noble metal nanoparticle layers, all the generated particle plasmon resonance signals are detected by the same detection unit, and it is noteworthy that the applicant named the optical fiber together with the noble metal nanoparticle layers as a sensor fiber 700. And preferably, the light source function generator 500 is electrically coupled to the detection unit 800, and transmits the function to the detection unit 800, so that the detection unit 800 can identify which detected particle plasmon resonance signal is from which light source in accordance with the detected particle plasmon resonance signals and the function. As a result, the multiplex fiber optic biosensor in accordance with the present invention only needs one detection unit 800, and identifies the type of light without using spectrometer.

In addition, a multiplex fiber optic biosensor in accordance with the present invention further provides the second means, namely, the lights with different wavelengths emitted by light sources propagate along the optical fiber in accordance with different carrier frequencies and the particle plasmon resonance signals are thereby generated.

Figure 5A:
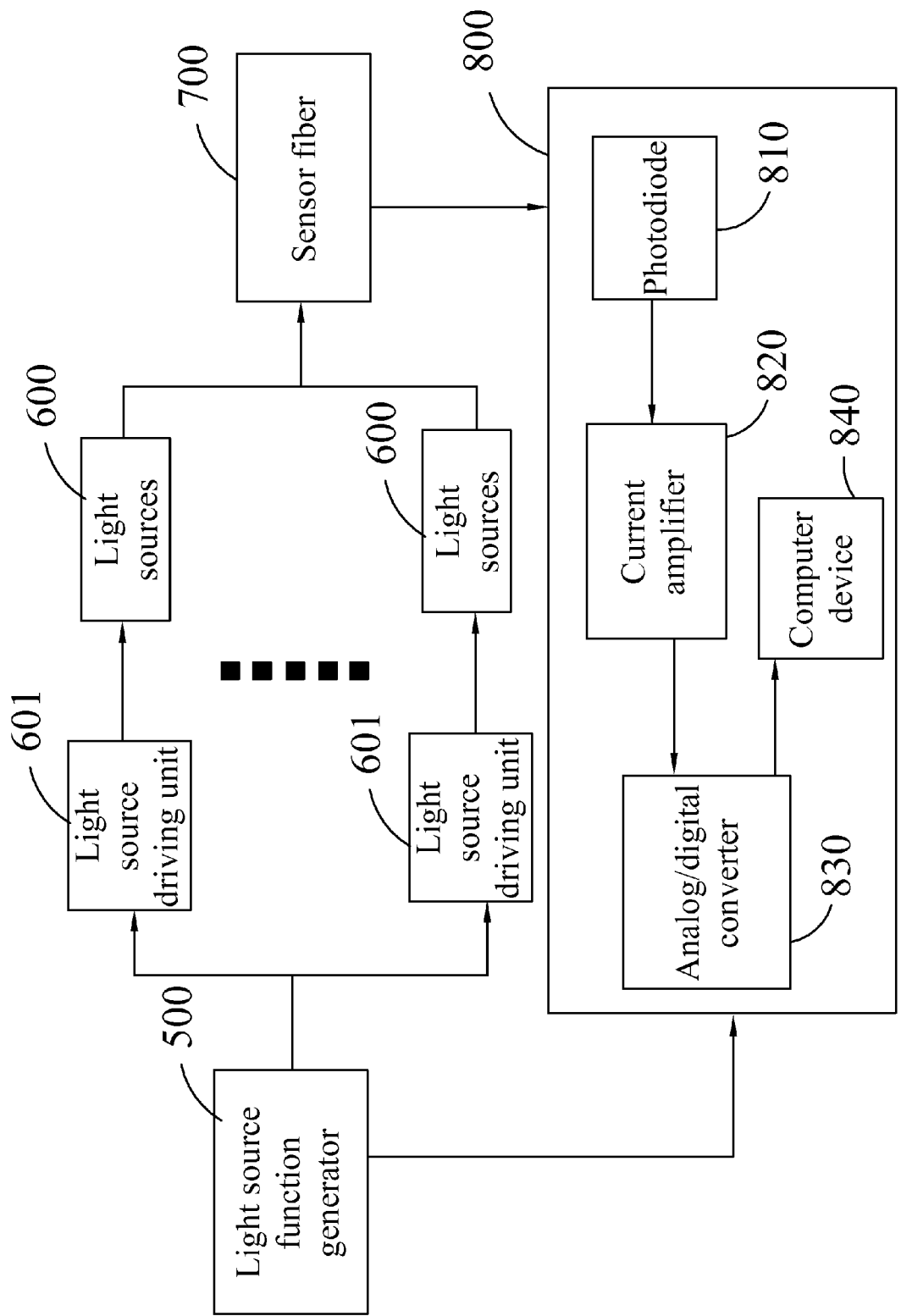
FIG. 5A is a schematic diagram showing the operation of a multiplex fiber optic biosensor in accordance with another exemplary embodiment of the present invention.
Figure 5B:
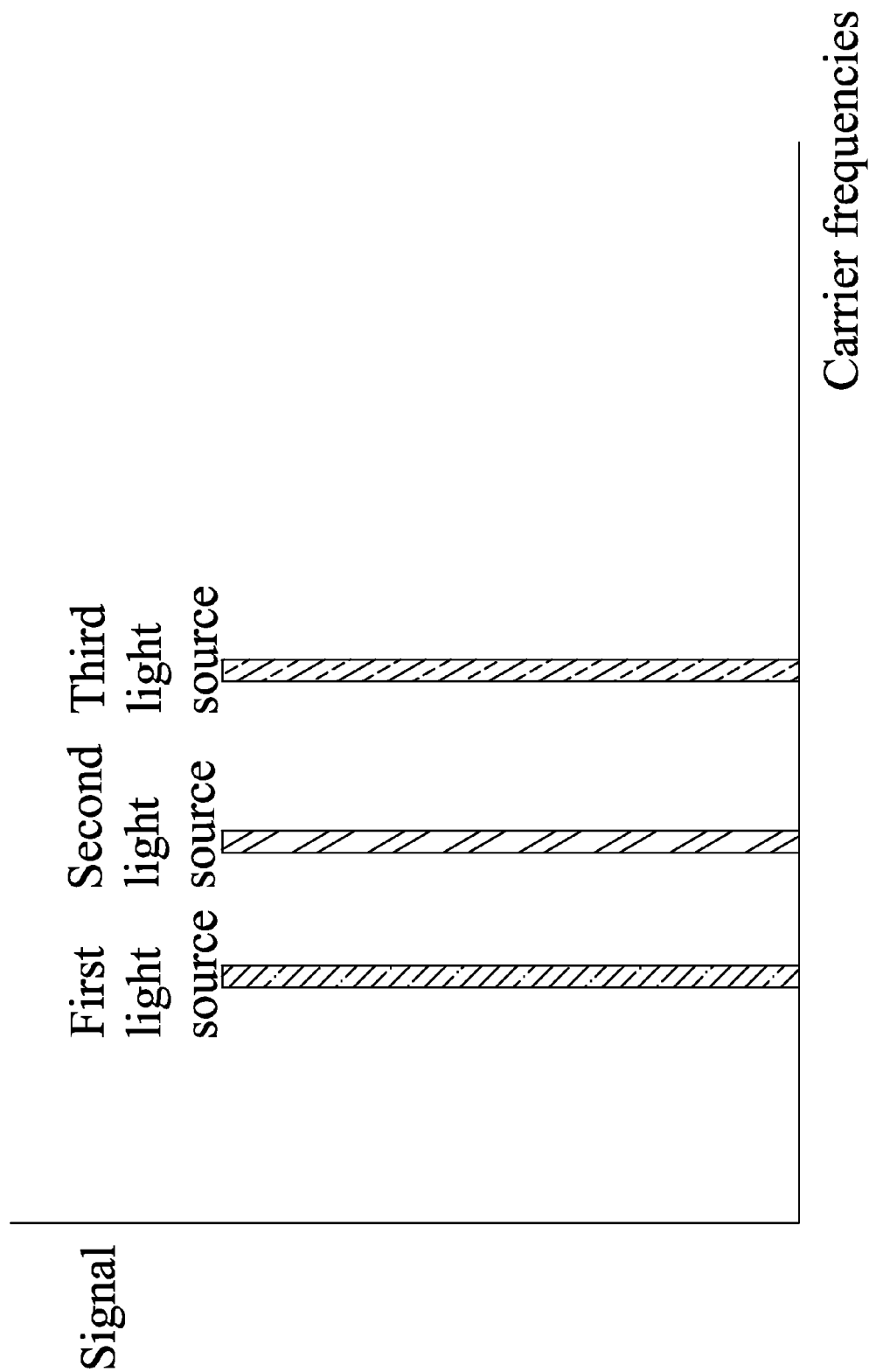
FIG. 5B is a schematic diagram showing the light sources of a multiplex fiber optic biosensor emit lights with different carrier frequencies in accordance with another exemplary embodiment of the present invention.
Figure 5C:
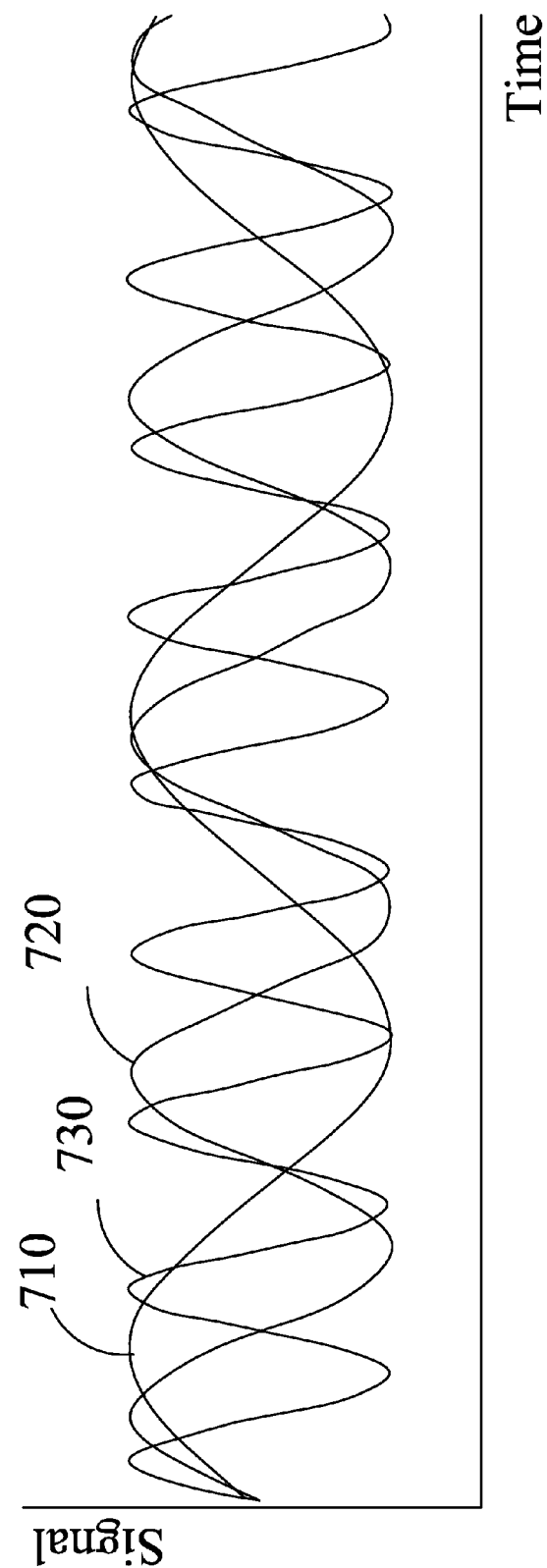
FIG. 5C is a schematic diagram showing the detection unit of a multiplex fiber optic biosensor receives particle plasmon resonance signals in accordance with another exemplary embodiment of the present invention.

With reference to FIGS. 5A to 5C. FIG. 5A is a schematic diagram showing the operation of a multiplex fiber optic biosensor in accordance with another exemplary embodiment of the present invention, FIG. 5B is a schematic diagram showing the light sources of a multiplex fiber optic biosensor emit lights with different carrier frequencies in accordance with another exemplary embodiment of the present invention and FIG. 5C is a schematic diagram showing the detection unit of a multiplex fiber optic biosensor receives particle plasmon resonance signals in accordance with another exemplary embodiment of the present invention. More specifically, the light source function generator 500 generates a function, so that the plurality of light sources 600 generate different carrier frequency signals based on the function, and preferably, the light sources 600 are electrically coupled to the light source driving unit 601, the light source driving unit 601 is electrically coupled to the light source function generator 500 to receive the function, so that the light sources 600 emit light by means of different carrier frequencies based on the function. While the lights propagate along the sensor fiber 700, the particle plasmon resonance signals are thereby produced by interactions between the noble metal nanoparticle layers and the corresponding analytes in the sensor fiber 700. For example, if the analyte has three components that needs to be analyzed, three different carrier frequencies for the emitting lights are needed, such as the first light source emits light via a first carrier frequency 710, the second light source emits light via a second carrier frequency 720 and a third light source emits light via a third carrier frequency 730. It is noteworthy that the three light sources emit light continuously according to the function and the carrier frequencies thereof are not the same. Similarly, the lights with different wavelengths are emitted by the three light sources in accordance with three different carrier frequencies, and each light is absorbed by the corresponding noble metal nanoparticle layer when the wavelength of the light matches the resonance wavelength of the noble metal nanoparticle layer, so as to generate three kinds of particle plasmon resonance signals.

Moreover, after the aforementioned three lights with different wavelengths passed through the sensor fiber 700, all the generated particle plasmon resonance signals are detected by the same detection unit 800, and preferably, the light source function generator 500 is electrically coupled to the detection unit 800 and transmits the function to the detection unit 800. Consequently, the detection unit 800 can identify which detected particle plasmon resonance signal is from which light source in accordance with the detected particle plasmon resonance signals and the function. As a result, the multiplex fiber optic biosensor in accordance with the present invention only needs one detection unit 800, and identifies the type of light without using spectrometer.

Figure 6:
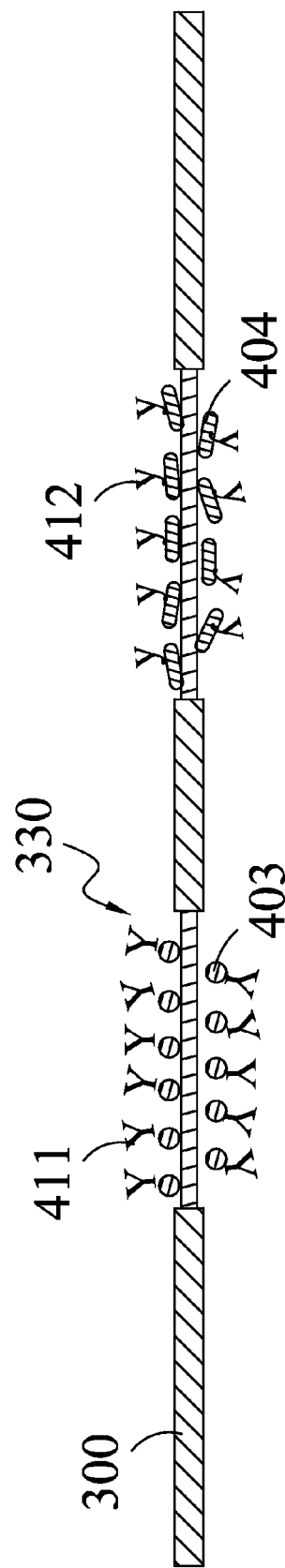
FIG. 6 is an experimental schematic diagram of a multiplex fiber optic biosensor in accordance with the present invention.

In order to verify the effect of the multiplex fiber optic biosensor in accordance with the present invention, the applicant further provides experimental data for reference. With reference to FIG. 6 for an experimental schematic diagram of a multiplex fiber optic biosensor in accordance with the present invention. Firstly, a silver nanoparticle layer 403 and a gold nanorod layer 404 are individually set on the sensing region 330 of the optical fiber 300, and 2,4-dinitrophenol (DNP) 411 and biotin 412 are respectively modified on the silver nanoparticle layer 403 and the gold nanorod layer 404.

Figure 7:
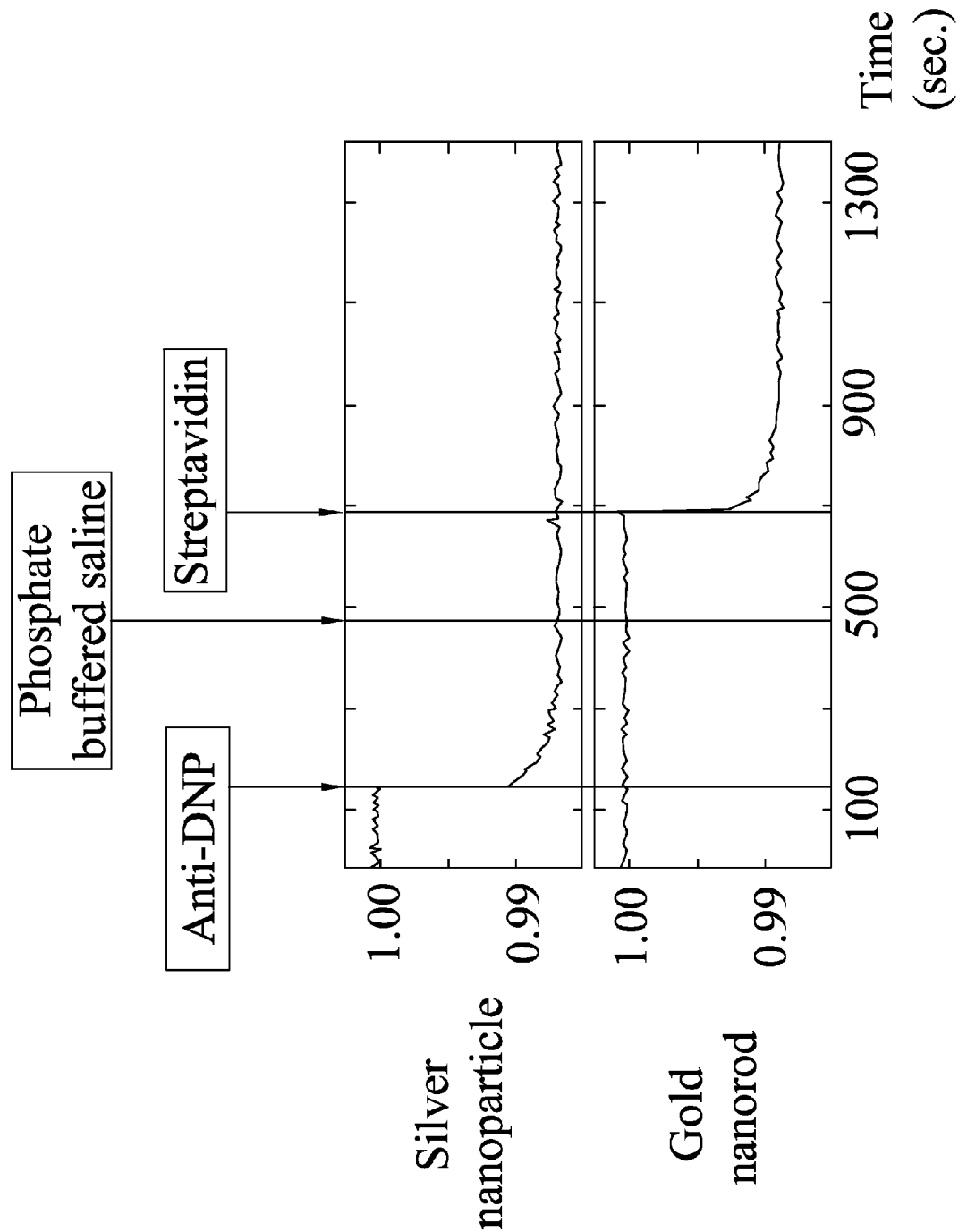
FIG. 7 is a diagram showing the results of a biosensing experiment conducted by different timing sequences in accordance with the present invention.

After the sensing is conducted by the multiplex fiber optic biosensor in accordance with the present invention, the results by using different timing sequences are shown in FIG. 7. FIG. 7 is a diagram showing the results of a biosensing experiment conducted by different timing sequences in accordance with the present invention. Firstly, when the anti-DNP solution is injected at the time of about 150 s, the silver nanoparticle region has obvious signal variation, but the gold nanorod region does not. When the phosphate buffered saline (PBS) is injected at the time of about 475 s and the streptavidin is injected at the time of about 690 s, the gold nanorod region has signal variation, but the silver nanoparticle region does not. Consequently, it can be demonstrated that the multiplex fiber optic biosensor in accordance with the present invention is feasible by using different timing sequences.

Figure 8:
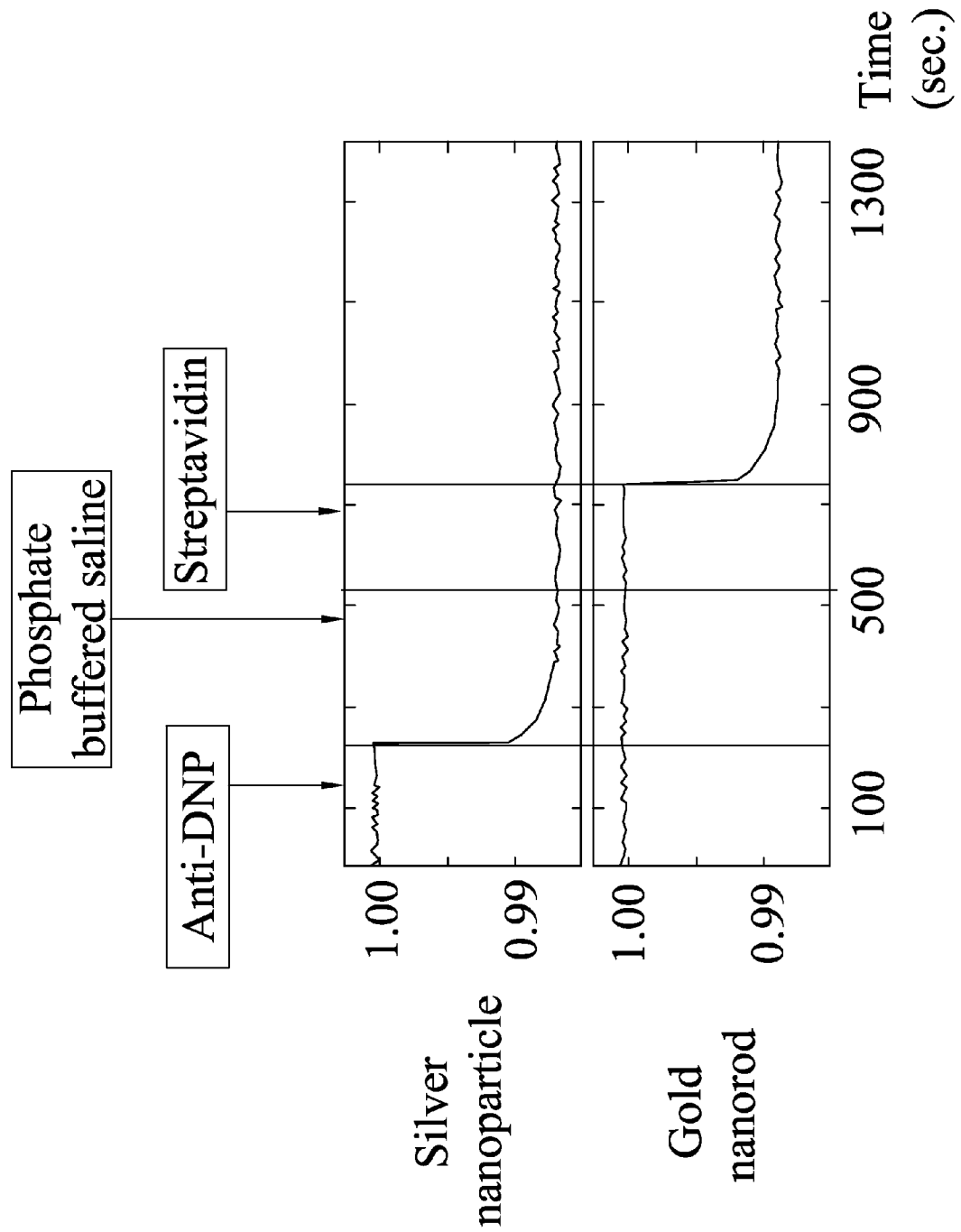
FIG. 8 is a diagram showing the results of a biosensing experiment conducted by different carrier frequencies in accordance with the present invention.

Besides, with reference to FIG. 8 for a diagram showing the results of a biosensing experiment conducted by different carrier frequencies in accordance with the present invention. After the sensing is conducted by the multiplex fiber optic biosensor in accordance with the present invention, the results by using different carrier frequencies are shown in FIG. 8. Firstly, when the anti-DNP solution is injected at the time of about 210 s, the silver nanoparticle region has obvious signal variation, but the gold nanorod region does not. Then, when the phosphate buffered saline (PBS) is injected at the time of about 550 s and the streptavidin is injected at the time of about 750 s, the gold nanorod region has signal variation, but the silver nanoparticle region does not. Consequently, it can be demonstrated that the multiplex fiber optic biosensor in accordance with the present invention is feasible by using different carrier frequencies.

Furthermore, the detection unit 800 mentioned in the multiplex fiber optic biosensor in accordance with the present invention preferably comprises a photodiode 810, a current amplifier 820, an analog/digital converter 830 and a computer device 840. Wherein, the photodiode 810 is used to detect the particle plasmon resonance signals, the current amplifier 820 is electrically connected to the photodiode 810 to amplify the light signal variation or the particle plasmon resonance signals, and the analog/digital converter 830 is electrically connected to the current amplifier 820. Because all the detected particle plasmon resonance signals belong to analog signals, the analog signals need to be transformed into digital signals when the particle plasmon resonance signals are analyzed via the computer device 840. Consequently, the analog/digital converter 830 is used to transform the particle plasmon resonance signals into digital signals; and the computer device 840 electrically connected to the current amplifier 820 receives and analyzes the particle plasmon resonance signals. And particularly, it is preferably that the computer device 840 receives the particle plasmon resonance signals by a universal serial bus (USB).

Figure 9:
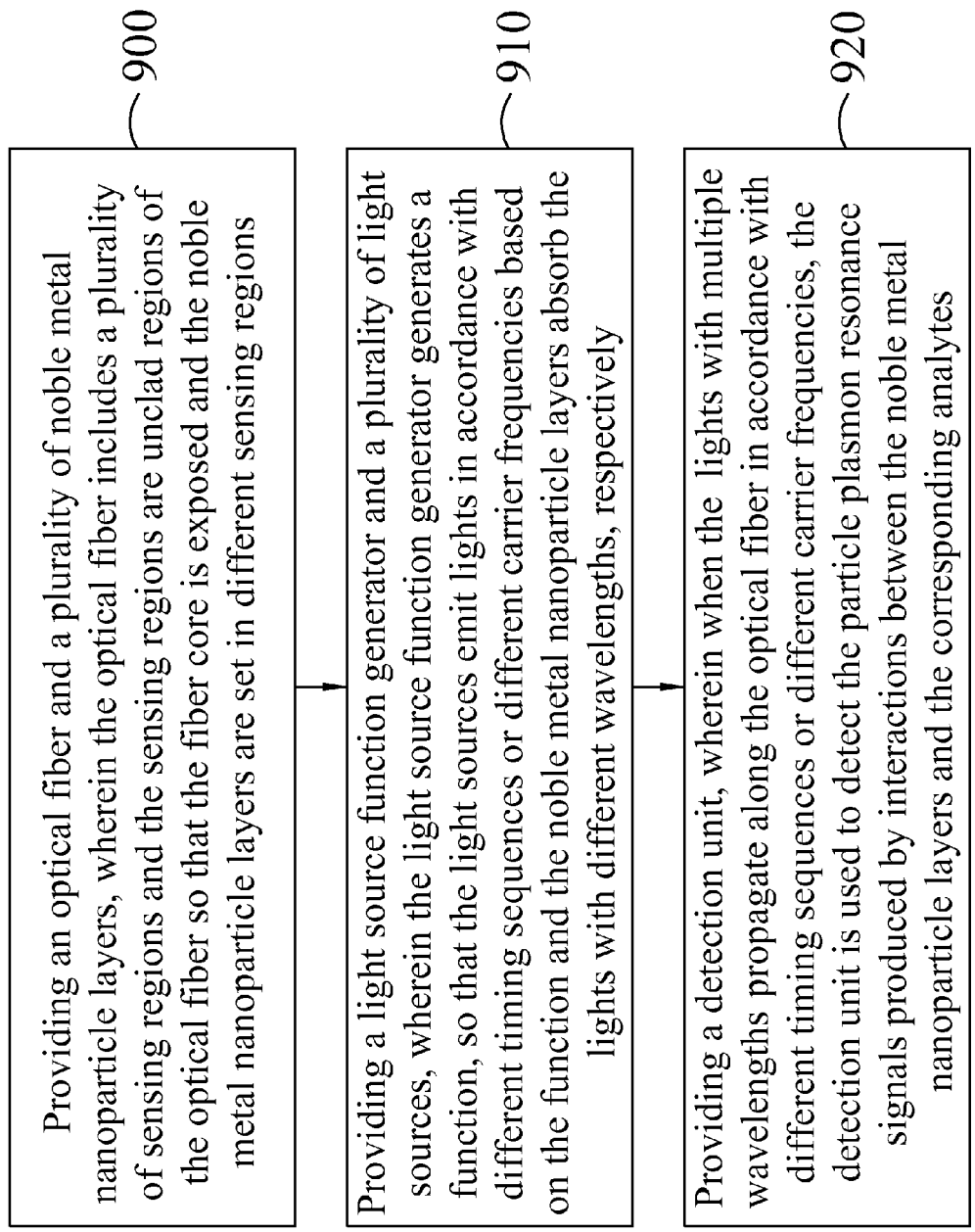
FIG. 9 is a flow chart showing a detection method of a multiplex fiber optic biosensor in accordance with the present invention.

With reference to FIG. 9 for a flow chart showing a detection method of a multiplex fiber optic biosensor in accordance with the present invention. The detection method of a multiplex fiber optic biosensor in accordance with the present invention comprises the following steps of: step 900 provides an optical fiber and a plurality of noble metal nanoparticle layers, wherein the optical fiber includes a plurality of sensing regions, and the sensing regions are unclad regions of the optical fiber so that the fiber core is exposed and the noble metal nanoparticle layers are set in different sensing regions; step 910 provides a light source function generator and a plurality of light sources, wherein the light source function generator generates a function, so that the light sources emit lights in accordance with different timing sequences or different carrier frequencies based on the function and the noble metal nanoparticle layers absorb the lights with different wavelengths, respectively; and step 920 provides a detection unit, wherein when the lights propagate along the optical fiber in accordance with the different timing sequences or the different carrier frequencies, the detection unit is used to detect the particle plasmon resonance signals produced by interactions between the different noble metal nanoparticle layers and the corresponding analytes.

While the means of specific embodiments in present invention has been described by reference drawings, numerous modifications and variations could be made thereto by those skilled in the art without departing from the scope and spirit of the invention set forth in the claims. The modifications and variations should in a range limited by the specification of the present invention.

What is claimed is:

1. A multiplex fiber optic biosensor, comprising:
    an optical fiber including a plurality of sensing regions, wherein the sensing regions are unclad regions of the optical fiber so that a fiber core of the optical fiber is exposed;
    a plurality of noble metal nanoparticle layers being set in the sensing regions;
    a plurality of light sources designed to emit lights with different wavelengths, and the noble metal nanoparticle layers absorbing the lights with different wavelengths, respectively, wherein each of the plurality of light sources corresponds to one of the sensing regions; and
    a light source function generator designed to generate a function for enabling the plurality of light sources continuously emitting the lights with different carrier frequencies in accordance with the function;
    wherein, when the lights propagate along the optical fiber in accordance with the different carrier frequencies, only one detector is used to detect particle plasmon resonance signals produced by interactions between the noble metal nanoparticle layers and corresponding analytes, wherein the light source function generator is electrically coupled to the detector and transmits the function to the detector, so as to analyze the particle plasmon resonance signals.

2. The multiplex fiber optic biosensor of claim 1, wherein the detector comprises:
    a photodiode detecting the particle plasmon resonance signals;
    a current amplifier electrically connected to the photodiode to amplify the particle plasmon resonance signals;
    an analog/digital converter electrically connected to the current amplifier to transform the particle plasmon resonance signals into digital signals; and
    a computer device electrically connected to the current amplifier to receive as well as analyze the particle plasmon resonance signals.

3. The multiplex fiber optic biosensor of claim 2, wherein the computer device receives the particle plasmon resonance signals by a universal serial bus (USB).

4. A multiplex fiber optic biosensor detection method, comprising the following steps:
    providing an optical fiber and a plurality of noble metal nanoparticle layers, wherein the optical fiber comprises a plurality of sensing regions, and the sensing regions are unclad regions of the optical fiber so that a fiber core of the optical fiber is exposed, and the noble metal nanoparticle layers are set in the sensing regions;
    providing a light source function generator and a plurality of light sources, wherein the light source function generator is designed to generate a function, so that the plurality of light sources continuously emit the lights with different carrier frequencies based on the function, and the noble metal nanoparticle layers absorb the lights with different wavelengths, respectively, wherein each of the plurality of light sources corresponds to one of the sensing regions; and
    providing only one detector, wherein, when the lights propagate along the optical fiber in accordance with the different carrier frequencies, the detector is used to detect particle plasmon resonance signals produced by interactions between the noble metal nanoparticle layers and corresponding analytes, wherein the light source function generator is electrically coupled to the detector and transmits the function to the detector, so as to analyze the particle plasmon resonance signals.

5. The multiplex fiber optic biosensor detection method of claim 4, wherein the detector comprises:
    a photodiode detecting the particle plasmon resonance signals;
    a current amplifier electrically connected to the photodiode to amplify the particle plasmon resonance signals;
    an analog/digital converter electrically connected to the current amplifier to transform the particle plasmon resonance signals into digital signals; and
    a computer device electrically connected to the current amplifier to receive as well as analyze the particle plasmon resonance signals.

6. The multiplex fiber optic biosensor detection method of claim 5, wherein the computer device receives the particle plasmon resonance signals by a universal serial bus (USB).

* * * * *